US006329191B1

(12) United States Patent
Ivy et al.

(10) Patent No.: US 6,329,191 B1
(45) Date of Patent: Dec. 11, 2001

(54) DNA ENCODING RECOMBINANT COFFEE BEAN ALPHA-GALACTOSIDASE

(75) Inventors: John M. Ivy, Kailua; David E. Clements, Honolulu, both of HI (US)

(73) Assignee: Hawaii Biotechnology Group, Inc., Aiea, HI (US)

( * ) Notice: Subject to any disclaimer, the term of this patent is extended or adjusted under 35 U.S.C. 154(b) by 0 days.

(21) Appl. No.: 08/113,890

(22) Filed: Aug. 30, 1993

(51) Int. Cl.$^7$ .............................. C12N 15/56; C12N 9/40
(52) U.S. Cl. ................................... 435/240.1; 435/252.3; 435/320.1; 435/208; 536/23.2
(58) Field of Search ..................... 536/23.2; 435/320.1, 435/240.1, 252.3, 69.1, 208

(56) References Cited

U.S. PATENT DOCUMENTS

| | | | |
|---|---|---|---|
| 4,330,619 | 5/1982 | Goldstein | 435/2 |
| 4,427,777 | 1/1984 | Goldstein | 435/240.2 |
| 4,609,627 | 9/1986 | Goldstein | 435/269 |
| 5,082,778 | 1/1992 | Overbeeke et al. | 435/172.3 |
| 5,179,023 | 1/1993 | Calhoun et al. | 435/320.1 |
| 5,296,365 | * 3/1994 | Overbeeke et al. | 435/208 |

FOREIGN PATENT DOCUMENTS

| | | |
|---|---|---|
| WO87/07641 | 12/1987 | (WO) . |
| WO90/11353 | 10/1990 | (WO) . |

OTHER PUBLICATIONS

Wieder et al., "Enzyme Therapy: II. Effect of Covalent Attachment of Polyethylene Glycol on Biochemical Parameters and Immunological Determinants of β–Glucosidase and α–Galactosidase", *Journal of Applied Biochemistry* 5:337–347 (1983).
Galfre et al., "Preparation of monoclonal antibodies: strategies and procedures", Methods of Enzymology 73:3–46 (1981).
Lenny, L.L., et al., Single–Unit Transfusions of RBC Enzymatically Converted from Group B to Group O and O Normal Volunteers; *Blood* (1991) 77:1383–1388.
Goldstein, J., et al., Group B Erythrocytes Enzymatically Converted to Group O Survive Normally in A, B, and O Individuals; *Science* (1982) 215:168–170.
Zarnitz, M.L., et al., Immunochemical Studies on Blood Groups. XXV. The Action of Coffee Bean α–Galactosidase on Blood Group B an BP1 Substances; *J Am Chem Soc* (1960) 82:3953–3957.
Harpaz, N., et al., Studies on B–Antigenic Sites of Human Erythrocytes by use of Coffee Bean α–Galactosidase; *Arch Biochem Biophys* (1975) 170:676–683.
Barham, D., et al., Studies on the Distribution of α–Galactosidases in Seeds; *Phytochem* (1971) 10:1759–1763.
Courtois, J.E., et al., α–Galactosidase from Coffee Beans; *Meth Enzymol* (1966) 8:565–571.
Harpaz, N., et al., Purification of Coffee Bean α–Galactosidase by Affinity Chromatography; *Biochem Biophys Acta* (1974) 341:213–221.
Hughes, S.G., et al., Messenger RNA from Isolated Aleurone Cells Directs the Synthesis of an α–Galactosidase Found in the Endosperm During Germination of guar (Cyamopsis tetragonaloba) Seed; *Plant Mol Biol* (1988) 11:783–789.
Overbeeke, N., et al., Cloning and Nucleotide Sequence of the α–Galactosidase cDNA from Cyamopsis tetragonaloba (guar); *Plant Mol Biol* (1989) 13:541–550.
Overbeeke, N., Secretion of the α–Galactosidase from Cyamopsis tetragonoloba (guar) by Bacillus subtilis; *Applied Environment Microbiol* (1990) 1429–1434.
Liljestrom, P.L., The Nucleotide Sequence of the Yeast MEL1 Gene; *Nucleic Acids Res* (1985) 13:7257–7269.
Sumner–Smith, M., et al., Analysis of the Inducible MEL1 Gene of Saccharomyces carlsbergensis and its Secreted Product, α–Galactosidase (melibiase); *Gene* (1985) 36:333–340.
Liljestrom, P.L., et al., Nucleotide Sequence of the melA Gene, Coding for α–Galactosidase in *E. coli* K–12; *Nucleic Acids Res* (1987) 15:2213–2220.
Calhoun, D.H., et al., Fabry Disease: Isolation of a cDNA Clone Encoding Human α–Galactosidase A; *Proc Natl Acad Sci USA* (1985) 83:7364–7368.
Bishop, D.F., et al., Human α–Galactosidase A: Nucleotide Sequence of a cDNA Clone Encoding the Mature Enzyme; *Proc Natl Acad Sci USA* (1986) 83:4859–4863).
Quinn, M., et al., A Genomic Clone Containing the Promoter for the Gene Encoding the Human Lysosomal Enzyme, α–Galactosidase A; *Gene* (1987) 58:177–188.
Dybus, S., *Transfusion* (1983) 23:244–247.
Harpaz, N., et al., *Eur J Biochem* (1977) 77:419–426.
Robsen et al. 1986. *Introduction to Protein Engineering*, Elsevier, New York, p. 41.*
Katsube et al. 1990. J Biochem 108:321–326.*
Woynez et al. 1990. Methods in Enzymology 182:738–749.*
Belyavsky et al. 1989. Nucleic Acids Res. 17(8): 2919–2932.*

* cited by examiner

*Primary Examiner*—Ponnathapu Achutamurthy
*Assistant Examiner*—Peter P. Tung
(74) *Attorney, Agent, or Firm*—Morrison & Foerster LLP

(57) ABSTRACT

A recombinant DNA encoding coffee bean α-galactosidase permits the production of purified forms of this protein. The protein is useful in converting human Type B red blood cells into cells physiologically similar to Type O red blood cells. The availability of this enzyme permits more effective conversion than use of α-galactosidase from other sources.

7 Claims, 4 Drawing Sheets

FIG. 1A

```
GATGACAGTTGGAGTAGCATGATGACTTCTCGGGCAGATATGAACGACAAATGGGCATCTTATGCTGGTCCCGGTGATGGAATGATCCAGACATGTTGGAGG    900
AspAspSerTrpSerSerMetThrSerArgAlaAspMetAsnAspLysTrpAlaSerTyrAlaGlyProGlyGlyTrpAspAsnAspProAspMetLeuGlu    219

TGGAAATGGAGGCATGACTACAACGGAATATCGATCCCATTTCAGCATTTGGGCATTAGCAAAAGCACCTCTGATTGGCTGTGACATTCGATCCAT          1000
ValGlyAsnGlyGlyMetTyrThrThrThrGluTyrArgSerHisPheSerIlePheTrpAlaLeuAlaLeuLysAlaProLeuLeuIleGlyCysAspIleArgSerMet  253

GGACGGTGCGACTTTCCAACTGCTAAGCAATGCGGAAGTTATTGCGGGTTAACCAAGATAAACTTGGCGTTCAAGGGAACAAGGTTAAGACTTACGGAGAT    1100
AspGlyAlaThrPheGlnLeuLeuSerAsnAlaGluValIleAlaGlyLeuThrLysIleAsnLeuGlyValGlnGlyAsnLysValLysThrTyrGlyAsp    286

TTGGAGGTTTGGGCTGGACCTCTTAGTGGAATAGAGTGCTGCGCTTTGTGGAATAGAGGATCTTCCACGGCTACTATTACCGCGTATTGGTCCGACG        1200
LeuGluValTrpAlaGlyProLeuSerGlyLysArgValAlaValAlaLeuTrpAsnArgGlySerSerThrAlaThrIleThrAlaTyrTrpSerAsp    319

TAGGCCTCCCGTCCACGGCAGTGGTAATGCACGAGACTTATGGGCGCATTCAACCGAAAAATCAGTCAAAGGACAAATCTCAGCTGCAGTAGATGCCCA     1300
ValGlyLeuProSerThrAlaValAlaValAsnAlaArgAspLeuTrpAlaHisSerThrGluLysSerValLysGlyInIleSerAlaAlaValAspAlaHis   353

CGATTCGAAAATGTATGTCCTAACCCCACAGTGATTAACAGGAGAATGCAGAAGACAAGTGATGGTTGGCTCTTTCAAGGATTTGATTACCTTAAAGAAT    1400
AspSerLysMetTyrValLeuThrProGlnEND
                              363

TTTTCACATGTTATGAATCAATTCAAAGCAATTATGTGTTTTGAAGAGATTAAGTCAATAAATAGAAAAGTTATTATTGAAAAAAAAAAAAAAAAAA       1544
```

FIG. 1B

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1497 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 72..1331

(ix) FEATURE:
      (A) NAME/KEY: mat_peptide
      (B) LOCATION: 243

(xi) SEQUENCE DESCRIPTION: SEQ ID NO:1:

```
CTTACCACTT CTAGGGGGCT CTGCTCCACA AAGCAGTGGC AATTGAGTTG ATTGATCAAC      60

ACCAATTTAC C ATG GCC GCT GCT TAT TAC TAC CTT TTT TCT AGT AAA AAA     110
             Met Ala Ala Ala Tyr Tyr Tyr Leu Phe Ser Ser Lys Lys
             -57     -55                 -50                 -45

AGC CAC CAA AAG CTG GTG CTC CGA GCT TCG TTA TTG ATG TTT TTA TGT      158
Ser His Gln Lys Leu Val Leu Arg Ala Ser Leu Leu Met Phe Leu Cys
            -40                 -35                 -30

TTC TTG GCG GTT GAA AAC GTT GGT GCT TCC GCT CGC GGG ATG GTG AAG      206
Phe Leu Ala Val Glu Asn Val Gly Ala Ser Ala Arg Arg Met Val Lys
        -25                 -20                 -15

TCT CCA GGA ACC GAG GAT TAC ACT CCC AGG AGC CTT TTA GCA AAT GGG      254
Ser Pro Gly Thr Glu Asp Tyr Thr Pro Arg Ser Leu Leu Ala Asn Gly
    -10                  -5                   1

CTT GGT CTA ACA CCT CCG ATG GGG TGG AAC AGC TGG AAT CAT TTC CGT      302
Leu Gly Leu Thr Pro Pro Met Gly Trp Asn Ser Trp Asn His Phe Arg
 5              10                  15                  20

TGT AAT CTT GAT GAG AAA TTG ATC AGG GAA ACA GCC GAT GCA ATG GTA      350
Cys Asn Leu Asp Glu Lys Leu Ile Arg Glu Thr Ala Asp Ala Met Val
                25                  30                  35

TCA AAG GGG CTT GCT GCA CTG GCA TAT AAG TAC ATC AAT CTT GAT GAC      398
Ser Lys Gly Leu Ala Ala Leu Ala Tyr Lys Tyr Ile Asn Leu Asp Asp
            40                  45                  50

TGT TGG GCA GAA CTT AAC AGA GAT TCA CAG GGG AAT TTG GTT CCC AAA      446
Cys Trp Ala Glu Leu Asn Arg Asp Ser Gln Gly Asn Leu Val Pro Lys
        55                  60                  65

GGT TCA ACA TTC CCA TCA GGG ATC AAA GCC TTA GCA GAT TAT GTT CAC      494
Gly Ser Thr Phe Pro Ser Gly Ile Lys Ala Leu Ala Asp Tyr Val His
    70                  75                  80

AGC AAA GGC CTA AAG CTT GGA ATT TAC TCT GAT GCT GGA ACT CAG ACA      542
Ser Lys Gly Leu Lys Leu Gly Ile Tyr Ser Asp Ala Gly Thr Gln Thr
85                  90                  95                 100

TGT AGT AAA ACT ATG CCA GGT TCA TTA GGA CAC GAA GAA CAA GAT GCC      590
Cys Ser Lys Thr Met Pro Gly Ser Leu Gly His Glu Glu Gln Asp Ala
                105                 110                 115

AAA ACC TTT GCT TCA TGG GGG GTA GAT TAC TTA AAG TAT GAC AAC TGT      638
Lys Thr Phe Ala Ser Trp Gly Val Asp Tyr Leu Lys Tyr Asp Asn Cys
            120                 125                 130

AAC AAC AAC AAC ATA AGC CCC AAG GAA AGG TAT CCA ATC ATG AGT AAA      686
Asn Asn Asn Asn Ile Ser Pro Lys Glu Arg Tyr Pro Ile Met Ser Lys
        135                 140                 145
```

-continued

```
GCA TTG TTG AAC TCT GGA AGG TCC ATA TTT TTC TCT CTA TGT GAA TGG        734
Ala Leu Leu Asn Ser Gly Arg Ser Ile Phe Phe Ser Leu Cys Glu Trp
    150                 155                 160

GGA GAG GAA GAT CCA GCA ACA TGG GCA AAA GAA GTT GGA AAC AGT TGG        782
Gly Glu Glu Asp Pro Ala Thr Trp Ala Lys Glu Val Gly Asn Ser Trp
165                 170                 175                 180

AGA ACC ACT GGA GAT ATA GAT GAC AGT TGG AGT AGC ATG ACT TCT CGG        830
Arg Thr Thr Gly Asp Ile Asp Asp Ser Trp Ser Ser Met Thr Ser Arg
                185                 190                 195

GCA GAT ATG AAC GAC AAA TGG GCA TCT TAT GCT GGT CCC GGT GGA TGG        878
Ala Asp Met Asn Asp Lys Trp Ala Ser Tyr Ala Gly Pro Gly Gly Trp
            200                 205                 210

AAT GAT CCA GAC ATG TTG GAG GTG GGA AAT GGA GGC ATG ACT ACA ACG        926
Asn Asp Pro Asp Met Leu Glu Val Gly Asn Gly Gly Met Thr Thr Thr
                215                 220                 225

GAA TAT CGA TCC CAT TTC AGC ATT TGG GCA TTA GCA AAA GCA CCT CTA        974
Glu Tyr Arg Ser His Phe Ser Ile Trp Ala Leu Ala Lys Ala Pro Leu
        230                 235                 240

CTG ATT GGC TGT GAC ATT CGA TCC ATG GAC GGT GCG ACT TTC CAA CTG       1022
Leu Ile Gly Cys Asp Ile Arg Ser Met Asp Gly Ala Thr Phe Gln Leu
245                 250                 255                 260

CTA AGC AAT GCG GAA GTT ATT GCG GTT AAC CAA GAT AAA CTT GGC GTT       1070
Leu Ser Asn Ala Glu Val Ile Ala Val Asn Gln Asp Lys Leu Gly Val
                265                 270                 275

CAA GGG AAC AAG GTT AAG ACT TAC GGA GAT TTG GAG GTT TGG GCT GGA       1118
Gln Gly Asn Lys Val Lys Thr Tyr Gly Asp Leu Glu Val Trp Ala Gly
            280                 285                 290

CCT CTT AGT GGA AAG AGA GTA GCT GTC GCT TTG TGG AAT AGA GGA TCT       1166
Pro Leu Ser Gly Lys Arg Val Ala Val Ala Leu Trp Asn Arg Gly Ser
        295                 300                 305

TCC ACG GCT ACT ATT ACC GCG TAT TGG TCC GAC GTA GGC CTC CCG TCC       1214
Ser Thr Ala Thr Ile Thr Ala Tyr Trp Ser Asp Val Gly Leu Pro Ser
310                 315                 320

ACG GCA GTG GTT AAT GCA CGA GAC TTA TGG GCG CAT TCA ACC GAA AAA       1262
Thr Ala Val Val Asn Ala Arg Asp Leu Trp Ala His Ser Thr Glu Lys
                325                 330                 335                 340

TCA GTC AAA GGA CAA ATC TCA GCT GCA GTA GAT GCC CAC GAT TCG AAA       1310
Ser Val Lys Gly Gln Ile Ser Ala Ala Val Asp Ala His Asp Ser Lys
                345                 350                 355

ATG TAT GTC CTA ACC CCA CAG TGATTAACAG GAGAATGCAG AAGACAAGTG          1361
Met Tyr Val Leu Thr Pro Gln
                360

ATGGTTGGCT CTTTCAAGGA TTTGATTACC TTAAAGAATT TTTCACATGT TATGAATCAA    1421

TTCAAAGCAA TTATGTGTTT TGAAGAGATT AAGTCAATAA ATAGAAAAGT TATTATTGAA    1481

AAAAAAAAAA AAAAAA                                                    1497

(2) INFORMATION FOR SEQ ID NO:2:

(i) SEQUENCE CHARACTERISTICS:
        (A) LENGTH: 420 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Ala Tyr Tyr Tyr Leu Phe Ser Ser Lys Lys Ser His Gln
-57         -55                 -50                 -45
```

-continued

```
Lys Leu Val Leu Arg Ala Ser Leu Leu Met Phe Leu Cys Phe Leu Ala
    -40                 -35                 -30

Val Glu Asn Val Gly Ala Ser Ala Arg Arg Met Val Lys Ser Pro Gly
-25         Asn     -20             -15                     -10

Thr Glu Asp Tyr Thr Pro Arg Ser Leu Leu Ala Asn Gly Leu Gly Leu
                -5                   1               5

Thr Pro Pro Met Gly Trp Asn Ser Trp Asn His Phe Arg Cys Asn Leu
        10                  15                  20

Asp Glu Lys Leu Ile Arg Glu Thr Ala Asp Ala Met Val Ser Lys Gly
        25                  30                  35

Leu Ala Ala Leu Ala Tyr Lys Tyr Ile Asn Leu Asp Asp Cys Trp Ala
40              45                  50                      55

Glu Leu Asn Arg Asp Ser Gln Gly Asn Leu Val Pro Lys Gly Ser Thr
                60                  65                  70

Phe Pro Ser Gly Ile Lys Ala Leu Ala Asp Tyr Val His Ser Lys Gly
            75                  80                  85

Leu Lys Leu Gly Ile Tyr Ser Asp Ala Gly Thr Gln Thr Cys Ser Lys
        90                  95                  100

Thr Met Pro Gly Ser Leu Gly His Glu Glu Gln Asp Ala Lys Thr Phe
    105                 110                 115

Ala Ser Trp Gly Val Asp Tyr Leu Lys Tyr Asp Asn Cys Asn Asn Asn
120             125                 130                     135

Asn Ile Ser Pro Lys Glu Arg Tyr Pro Ile Met Ser Lys Ala Leu Leu
                140                 145                 150

Asn Ser Gly Arg Ser Ile Phe Phe Ser Leu Cys Glu Trp Gly Glu Glu
            155                 160                 165

Asp Pro Ala Thr Trp Ala Lys Glu Val Gly Asn Ser Trp Arg Thr Thr
        170                 175                 180

Gly Asp Ile Asp Asp Ser Trp Ser Ser Met Thr Ser Arg Ala Asp Met
    185                 190                 195

Asn Asp Lys Trp Ala Ser Tyr Ala Gly Pro Gly Gly Trp Asn Asp Pro
200             205                 210                     215

Asp Met Leu Glu Val Gly Asn Gly Gly Met Thr Thr Thr Glu Tyr Arg
            220                 225                 230

Ser His Phe Ser Ile Trp Ala Leu Ala Lys Ala Pro Leu Leu Ile Gly
        235                 240                 245

Cys Asp Ile Arg Ser Met Asp Gly Ala Thr Phe Gln Leu Leu Ser Asn
    250                 255                 260

Ala Glu Val Ile Ala Val Asn Gln Asp Lys Leu Gly Val Gln Gly Asn
265                 270                 275

Lys Val Lys Thr Tyr Gly Asp Leu Glu Val Trp Ala Gly Pro Leu Ser
280             285                 290                     295

Gly Lys Arg Val Ala Val Ala Leu Trp Asn Arg Gly Ser Ser Thr Ala
            300                 305                 310

Thr Ile Thr Ala Tyr Trp Ser Asp Val Gly Leu Pro Ser Thr Ala Val
        315                 320                 325

Val Asn Ala Arg Asp Leu Trp Ala His Ser Thr Glu Lys Ser Val Lys
    330                 335                 340

Gly Gln Ile Ser Ala Ala Val Asp Ala His Asp Ser Lys Met Tyr Val
    345                 350                 355

Leu Thr Pro Gln
360
```

DNA ENCODING RECOMBINANT COFFEE BEAN ALPHA-GALACTOSIDASE

TECHNICAL FIELD

The invention is directed to recombinant production of coffee bean α-galactosidase for use in modifying human red blood cells. More specifically, the invention concerns a recombinant enzyme useful in the conversion of Type B red blood cells to cells having the physiological effect of Type O.

BACKGROUND ART

The desirability of obtaining "universal donor"-type red blood cells for transfusion is well recognized. Red blood cells of the "O" type—i.e., lacking both the "A" and "B" antigenic determinants—are suitable. Treatment of the Type A antigenic determinant with N-acetylgalactoseaminidase to destroy its antigenicity has been disclosed in U.S. Pat. No. 4,609,627. Of more relevance to the present invention, the use of coffee bean α-galactosidase for the conversion of Type B antigen to the antigenic equivalent of Type O has also been described by Goldstein in U.S. Pat. Nos. 4,330,619 and 4,427,777. Also describing this work are papers by Lenny, L. L., et al., *Blood* (1991) 77:1383–1388, and by Goldstein, J., et al., *Science* (1982) 215:168–170.

In the work by the Goldstein group, it was found necessary to equilibrate the erythrocytes to a pH of about 5.7–5.8 before contacting the erythrocytes with the α-galactosidase. This equilibration was found to prevent the hemolysis noted in attempts to remove the terminal galactose residue from the B determinant using conditions similar to those reported by Zarnitz, M. L., et al., *J Am Chem Soc* (1960) 82:3953–3957, and by Harpaz, N., et al., *Arch Biochem Biophys* (1975) 170:676–683. These earlier conversions had been conducted at a pH of about 5.

The coffee bean α-galactosidase utilized in the foregoing studies in U.S. Pat. Nos. 4,330,619 and 4,427,777 is apparently equivalent in purity to the commercially available α-galactosidase (EC 3.2.1.22) marketed by Boehringer Mannheim. Further purification by undisclosed methods may have been conducted by Goldstein (1982) supra and Lenny (1991) supra. The molecular weight of coffee bean α-galactosidase was reported to be 26 kD by Barham, D., et al., *Phytochem* (1971) 10:1759–1763. The α-galactosidase can be purified using affinity chromatography with a substrate or substrate analog, as described by Courtois, J. E., et al., *Meth Enzymol* (1966) 8:565–571, and by Harpaz, N., et al., *Biochem Biophys Acta* (1974) 341:213–221. As shown hereinbelow, the commercial preparation of coffee bean α-galactosidase available is, in fact, an impure mixture of at least four proteins; only a vanishingly small amount of this preparation has the molecular weight 26 kD. In general, the readily detectable proteins in the mixture have molecular weights of 68 kD (40%), 40 kD (35%) and 36 kD (10%); the 68 kD protein is BSA added as a stabilizer. The 40 kD protein has the α-galactosidase activity and corresponds in molecular weight to the deduced amino acid sequence as described below.

The work of Goldstein et al. cited above indicates that coffee bean α-galactosidase is the enzyme of choice for the conversion of B antigen on erythrocytes to that consistent with universal donor erythrocytes. Although it is thus clear that coffee bean α-galactosidase is desirable for this conversion, practical sources for pure preparations of this enzyme for such use have not been available.

The genes or cDNAs encoding α-galactosidases from other sources have been retrieved and reported. These enzymes are not as effective for the degalactosylation of B antigen. Most closely related to the α-galactosidase of the invention is the enzyme from the legume guar (*Cyamopsis tetragonaloba*) seed. (See Hughes, S. G., et al., *Plant Mol Biol* (1988) 11:783–789; Overbeeke, N., et al., *Plant Mol Biol* (1989) 13:541–550; and PCT Application WO87/07641.) The cDNA encoding the guar α-galactosidase has been expressed and the protein secreted from *B. subtilis*, as reported by Overbeeke, N., *Applied Environment Microbiol* (1990) 1429–1434. This enzyme, however, has the disadvantage of a considerably lower pH optimum than that of coffee bean α-galactosidase. Retrieval of α-galactosidase-encoding cDNA from coffee bean by methods analogous to those used for the guar enzyme cDNA is not possible, since in the guar seed α-galactosidase is synthesized in the aleurone layer during germination and an aleurone layer is lacking in coffee beans. Accordingly, the procedures followed in obtaining guar messenger RNA encoding α-galactosidase cannot be followed in coffee bean.

Other sources of α-galactosidase also are known, and the genes or cDNAs have been cloned in some cases. The gene encoding the α-galactosidase of yeast has been reported by Liljestrom, P. L., *Nucleic Acids Res* (1985) 13:7257–7269; Sumner-Smith, M., et al., *Gene* (1985) 36:333–340. The DNA encoding the enzyme from *E. coli* is described by Liljestrom, P. L., et al., *Nucleic Acids Res* (1987) 15:2213–2220. Human α-galactosidase A has been implicated in Fabry disease, and cDNA encoding this protein has been isolated (Calhoun, D. H., et al., *Proc Natl Acad Sci USA* (1985) 83:7364–7368; Biship, D. F., et al., *Proc Natl Acad Sci USA* (1986) 83:4849–4853). A genomic clone containing the promoter for this gene was reported by Quinn, M., et al., *Gene* (1987) 58:177–188, and the recombinant enzyme has been suggested as a treatment for Fabry disease, as set forth in PCT Application WO90/11353 and U.S. Pat. No. 5,179,023.

None of these genes appears suitable for the production of α-galactosidase for use in the conversion of B erythrocytes, since this range of enzymes has considerable variance in substrate specificity and differences in pH optima. For example, Overbeeke et al. (1987 PCT Application WO87/07641) demonstrate that α-Gals of plant origin (guar, fenugreek, lucerne, and coffee beans) are able to reduce the galactose content of galactomannans, whereas microbial (*Aspergillus niger, Saccharomyces carlsbergensis*, and *Escherichia coli*) α-Gals lack this enzymatic capability. Although it has been shown that α-galactosidase from *Clostridium sporogenes* (Dybus, S., *Transfusion* (1983) 23:244–247) and from soybeans (Harpaz, N., et al., *Eur J Biochem* (1977) 77:419–426) can remove the terminal galactose from B-antigen, these enzymes are more complex and the pH optima appear to be too low to effect the desired conversion on erythrocytes, since at low pH values, hemolysis occurs.

Thus, the present invention provides, for the first time, a practical source for purified and isolated coffee bean α-galactosidase required for the conversion of B-type red blood cells to red blood cells capable of serving as universal donors.

DISCLOSURE OF THE INVENTION

The invention is directed to the recombinant production of coffee bean α-galactosidase (coffee bean α-Gal). The production of this protein in recombinant form permits the practical production of sufficient quantities of pure enzyme for use in effecting the production of universal donor red blood cells.

Thus, in one aspect, the invention is directed to DNA encoding coffee bean α-galactosidase having the amino acid sequence shown in FIG. 1 herein or α-galactosidase encoded by the allelic variants of its encoding DNA. The invention is also directed to expression systems for the production of this protein and to methods for its production using these systems.

In other aspects, the invention is directed to methods to manufacture universal donor red blood cells by treating red blood cells containing Type B antigen with the recombinant enzyme of the invention, to antisense and triple helix-forming oligomers, and to antibodies specific for coffee bean α-Gal.

BRIEF DESCRIPTION OF THE DRAWINGS

FIG. 1 (SEQ ID NO: 1 and SEQ ID NO: 2) shows the DNA encoding coffee bean α-galactosidase and the deduced amino acid sequence of the enzyme. The DNA includes a region encoding a preprosequence numbered (−57)–(−1), as well as the sequence encoding the mature protein, designated positions (+1)–(363).

MODES OF CARRYING OUT THE INVENTION

Figure 2:
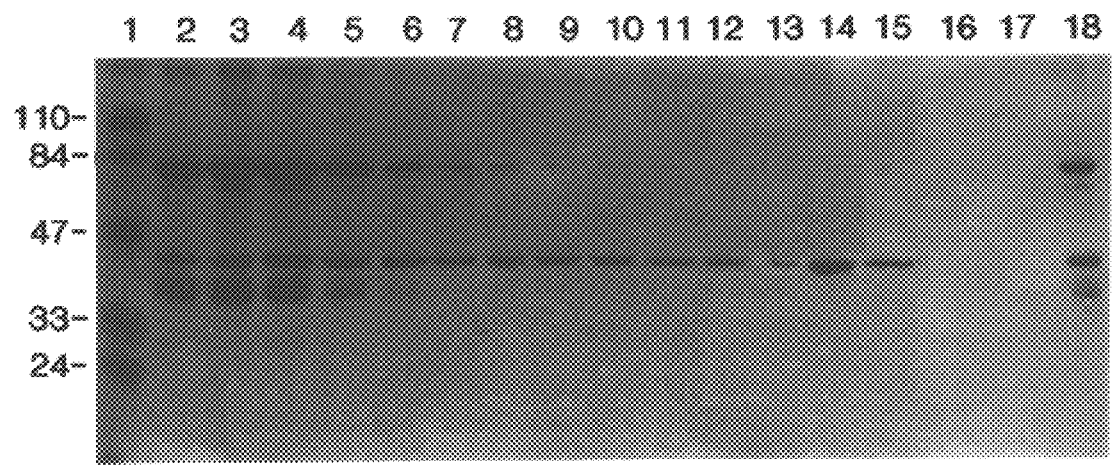
FIG. 2 shows the results of melibiose-affinity chromatography purification of coffee bean α-galactosidase as monitored by SDS-PAGE.

Coffee bean α-galactosidase (coffee bean α-Gal) is provided in recombinant form permitting sufficient quantities of purified enzyme to be produced for its practical use in treatment of red blood cells containing the B antigen. By "coffee bean α-galactosidase" is meant a protein having the ability to remove the terminal α-galactose from the B antigen, which has the amino acid sequence shown for the mature protein (numbered 1–363) in FIG. 1 herein. Also included in the definition are proteins having this activity which are encoded by DNAs that are allelic variants of the DNA shown in FIG. 1 as encoding the mature protein. As allelic variants are very similar in sequence to each other, the availability of the DNA of FIG. 1 provides probes which can readily retrieve such variants.

It is also recognized that minor variations in amino acid sequence, such as one or two deletions, substitutions, additions, or other modifications can generally be made without affecting the activity of a protein. Accordingly, "coffee bean α-galactosidase" as defined herein, includes such variants, as well as fragments of the 363-amino acid sequence shown which retain activity.

Described in the examples below is the retrieval of the cDNA encoding coffee bean α-galactosidase. As it occurs in the bean, the mature enzyme is produced as a preproenzyme with an upstream sequence of 57 amino acids. Analogies with other preproenzymes suggest a signal protease cleavage site between residues (−20) and (−19); thus, the secretion signal would constitute residues (−57)–(−20) to yield a proenzyme of the sequence shown at (−19) to 363. The mature protein contains 363 amino acids, as verified by the N-terminal sequence of the isolated mature protein described in the examples below.

In addition to providing recombinant materials for the production of the enzyme, the invention makes available the native nucleic acid sequences encoding coffee bean α-Gal. The sequences provide the information required to design oligonucleotides which regulate the production of this enzyme. The native sequence can be used as a basis for such design per se or can be used as a probe to retrieve additional portions of the DNA region which effects coffee bean α-Gal production. These additional portions can also be used for such design. These oligomers may be "antisense" oligomers which are complementary to the single strand encoding these proteins or to the related regulatory sequences included in the RNA and/or DNA, or may be capable of forming triple helices with the duplex gene either in the coding region or in the regulatory regions thereof.

The availability of the purified enzyme also permits the preparation of antibody compositions which consist of antibodies immunoreactive with the enzyme. In addition to providing suitable immunogens, the purified enzyme can be used as a reagent to isolate compositions wherein all contained antibodies are immunoreactive with the enzyme.

General Description and Definitions

The practice of the present invention will employ, unless otherwise indicated, conventional biochemistry, immunology, molecular biology and recombinant DNA techniques within the skill of the art. Such techniques are explained fully in the literature. See, e.g., Maniatis et al., Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The following terminology will be used in accordance with the definitions set out below in describing the present invention.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" control sequences when expression of said coding sequences is effected when the expression system is contained in an appropriate host cell.

A "host cell" is a cell which has been modified to contain, or is capable of modification to contain, an exogenous DNA sequence.

Antibodies which are "specifically immunoreactive" with a referent antigen refers to antibodies which are capable of binding to such antigen with a perceptibly greater affinity as compared to the ability to bind other antigens. The level of difference in affinity required depends on the nature of the application. Preferably, the referred-to antigen is bound with an affinity at least ten time greater than that descriptive of binding to a contaminant and more preferably with 100 times more affinity.

When the enzyme of the invention is described as being in "purified and isolated" form, the enzyme is described in a state wherein the composition in which it resides is at least 90% by weight composed of the enzyme, preferably 95% by weight and more preferably 99% by weight with respect to the organic components of the preparation.

Recombinant Production

The availability of the gene encoding coffee bean α-galactosidase permits the efficient production of the recombinant material. The desired coding sequence—that of the effective fragment, mature protein, proenzyme, or preproenzyme, or fragments thereof—is ligated into suitable expression systems for recombinant production. A wide variety of such expression systems and corresponding host cells is by now known in the art. The desired active protein may be produced intracellularly or secreted, depending on whether or not suitable secretory leader sequences are included in the expression system. Further, the active protein may be produced in the form of a fusion protein which may be active per se or which may be cleaved to yield the desired enzyme. All of these variations are by now standard in the art. Suitable expression systems include both bacterial systems and eucaryotic systems, including those of yeast, mammalian cells, insect cells and plants.

In more detail, the coffee bean α-Gal of the invention can be produced by constructing an expression system and modifying a host cell to contain this system to provide a cell line or culture capable of expressing DNA encoding the enzyme. DNA encoding the enzyme or active fragments can either be prepared directly by synthetic methods based on the native sequence (or equivalent sequences encoding the same amino acids), or by using the native sequence to design oligonucleotide probes to retrieve the coding sequence using known techniques. See, e.g., Mayfield et al, *J Virol* (1983) 4:259–264. The coding sequence can be comprised entirely of the mature protein-encoding sequences, or such sequences can be fused to other sequences (e.g., leader sequences) so that a fusion protein is encoded. See, e.g., U.S. Pat. Nos. 4,431,739; 4,425,437; 4,338,397. Synthetic coding sequences will also allow for the convenient construction of coding sequences which express coffee bean α-Gal modified as described above. Alternatively, coding sequences for these modified forms can be prepared by site-directed mutagenesis of native nucleotide sequences. The techniques of site-directed mutagenesis are known in the art.

To complete construction of an expression system, the coding sequence as described above for the coffee bean α-Gal is then operably linked to control sequences (e.g., a promoter, etc.), so that the DNA sequence encoding the enzyme is transcribed into messenger RNA in the host cell modified to contain the expression system.

For expression in a procaryotic, yeast or mammalian cell, the promoter and other control sequences are usually heterologous to the enzyme-encoding sequence. The expression system may be constructed as a discrete molecular entity flanked by convenient restriction sites; alternatively, it may be constructed by inserting the coding sequence into a previously constructed expression vector with an appropriate insertion site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Publication Nos. GB2,121,054; GB2,008,123; GB2,007,675; and European Publication No. 103,395. Preferred procaryotic expression vectors are those for *E. coli*. Yeast expression vectors are also known in the art. See, e.g., U.S. Pat. Nos. 4,446,235; 4,443,539; 4,430,428; see also European Publication Nos. 103,409; 100,561; 96,491.

Expression may also be achieved in mammalian cells. Appropriate mammalian expression hosts include kidney cell lines (e.g., CV-1 monkey kidney cell lines), fibroblast cell lines, Chinese hamster ovary (CHO) cells, HeLa cells, mouse NIH/3T3 and/or LMTK$^{31}$ cells. Alternatively, the coffee bean α-Gal may be expressed in myeloma cell lines employing immunoglobulin promoters. See, e.g., Banerjle et al. *Cell* (1983) 33:729–740; U.S. Pat. No. 4,663,281. Mammalian expression vectors employing viral promoters (e.g., SV40 early region promoter, Rous sarcoma virus, LTR promoter, etc.) are also well known in the art. See, e.g., Pachl et al., *J Virol* (1987) 61:315–325; Gorman et al., *Proc Natl Acad Sci USA* (1982) 79:6777– 6781; Southern et al., *J Mol App Genet* (1982) 1:327–341; PCT Publication No. WO87/02062. Preferred eucaryotic expression vectors employ the vaccinia virus, the SV40 virus, or the Rous sarcoma virus. See, e.g., Mackett et al., *J Virol* (1984) 49:857; DNA Cloning, vol. II, pp. 191–211, supra; PCT Publication No. WO86/07593; Chakrabarty et al., *Mol Cell Biol* (1985) 5:403.

A host cell that has been stably transformed by an expression system for the enzyme is then selected to produce the recombinant coffee bean α-Gal.

Thus, the expression systems are constructed using standard recombinant techniques of restriction enzyme cleavage, modification, if necessary, effected by site-directed mutagenesis, and ligation. The expression systems are amplified using cloning or the polymerase chain reaction (PCR) and included in vectors suitable for modifying host cells so as to contain the expression systems of the invention. Once such modified hosts are obtained, the cells are cultured under conditions appropriate for the choice of host and under conditions wherein the control sequences contained in the expression systems effect the expression of the encoding DNA. The recombinant coffee bean α-galactosidase produced is then recovered from the culture and purified using standard techniques such as affinity chromatography, ion-exchange chromatography, reverse-phase chromatography, and the like.

Use and Industrial Applicability

The purified enzyme is then available for use in removal of the terminal α-galactose from B antigen. Application of the enzyme for this purpose is described according to the methods of Goldstein et al., supra. In general, the method involves preequilibration of the red blood cells to a pH of 5.7–5.8 followed by treatment with the enzyme for suitable time periods and recovery of the red blood cells, restoring them to physiological pH.

Red blood cells suitable for use in the method of the invention include those bearing B antigens,—i.e. Type B as well as Type AB red blood cells. In the case of AB antigen-characterized red blood cells, additional treatment with N-acetylgalactosaminidase is required to remove the A antigen in order to obtain a universal donor cell.

In addition to the use of the coffee bean α-Gal enzyme of the invention to produce universal donor cells as described above, the recombinant enzyme provides an adequate supply for other uses. For example, U.S. Pat. No. 5,179,023 discloses the use of α-galactosidase in the treatment of Fabry's Disease. α-Galactosidase is also used to reduce the content of galactomannans in various foodstuffs. See, for example, Japanese applications JP 61/274695; JP 12/47050; JP 12/47061. α-Galactose has also been used for the treatment o guar gum—i.e. galactomannan—to reduce the galactose content and alter physical properties of foodstuffs as disclosed in PCT application WO87/0764 1. The use of α-galactosidase to hydrolyze raffinose has been disclosed with respect to sugar beet extract. Porter, J. E., et al., "Ion exchange and affinity chromatography in the scaleup of purification of alpha-galactosidase from soybeans,", *Biotech Bioeng.*, vol. 37 (1991), pp. 356–363; Overbeeke, N., et al., "Cloning and Nucleotide Sequence of the α-Galactosidase cDNA from Cyantopsis tetragonaloba (guar)," *Plant Mol Biol.*(1989), vol. 13, pp. 541–550. It has also been used to make raffinose available for more complete utilization of molasses as a fermentation feedstock as disclosed in European application 241044.

The use of α-galactosidase to treat foods or as a dietary supplement to destroy components that cause flatulence has also been described by Porter, et al. (1990) supra and Overbeeke, et al. (1989) supra and in PCT application WO90/14101.

Thus, the coffee bean α-Gal of the invention has a multiplicity of uses. All of them benefit from the availability of recombinant forms of coffee bean α-Gal.

Regulation of Expression

It may be desirable to regulate the expression of coffee bean α-Gal in its native environment or in the recombinant host. The invention provides the native DNA sequence encoding mature or preproenzyme of coffee bean α-Gal which makes possible the design of suitable antisense and triple helix-forming oligonucleotides that can interrupt the expression of the gene.

Antisense oligonucleotides are generally designed as complements to the messenger RNA encoding the desired protein. The complement binds through Watson-Crick base-pairing to the mRNA interfering with translation either by enhancing mRNA degradation by RNAse H, by preventing or inhibiting processing to mature RNA, or by preventing translation. The oligonucleotide may bind either to the translated region or to control sequences in the mRNA.

Similarly, as the transcription of DNA involves partial disassembly of the double helix, antisense oligonucleotides may also bind to transcribed or nontranscribed regions of the DNA to inhibit transcription. Absolute homology between the target and the antisense sequences is preferred but not required for the inhibition. Holt, J. T. et al., *Proc Natl Acad Sci* (1986) 83:4794.

Oligonucleotides may also be designed to form a triplex DNA structure with the intact duplex gene according to certain binding rules. Moffat, A. S., *Science* (1991) 252: 1374–1375. When this triplex structure is formed in the promoter region of a gene, it has been shown to disrupt transcription of that gene. Orson, F. M. et al., *Nuc Acids Res* (1991) 19:3435–3441. Again, the oligomer designed to form a triplex can be designed to bind the duplex gene in either regulatory or transcribed regions or both.

The invention, therefore, also includes methods and compositions useful to regulate the production of the coffee bean enzyme by use of the antisense or triple helix-forming techniques. The relevant oligomers may be delivered to cells containing the expression systems or to the native developing coffee bean.

Preparation of Antibodies

The production of polyclonal and monoclonal antibodies reactive with the purified enzyme is within the skill of the art. A mammal, such as a mouse, is immunized with the enzyme, or a fragment or a precursor containing the relevant epitopes. The serum may be harvested as a polyclonal composition. The availability of purified coffee bean α-Gal makes possible the production of compositions of antibodies substantially all of which bind this enzyme or its precursors. Standard immunoaffinity chromatography techniques can be employed for this purpose. The resulting compositions are useful in quality control assays for preparation of the enzyme as well as in assay methods for levels of coffee bean α-gal as an index to seed development.

Antibody-producing B lymphocytes can also be recovered from the animal and immortalized by, for example, fusion with a continuous cell line to produce an immortal antibody-producing cell line; i.e., a hybridoma, trioma, etc. Immortal, antibody-producing cell lines can also be created by techniques other than fusion, such as direct transformation of B-lymphocytes with oncogenic DNA, or transfection with Epstein-Barr virus. See, e.g., M. Schreier et al., Hybridoma Techniques (1980); Hammerling et al., Monoclonal antibodies and T-Cell Hybridomas (1981); Kennett et al., Monoclonal Antibodies (1980); see also U.S. Pat. Nos. 4,341,761; 4,399,121; 4,427,783; 4,444,887; 4,451,570, 4,466,917; 4,472,500; 4,491,632; 4,493,890. After screening, monoclonal antibody is harvested from the immortalized cell lines utilizing conventional separation and purification techniques.

The antibodies thus prepared are useful in purification procedures for isolation of highly purified coffee bean α-Gal and for assessing levels of this enzyme in situ.

The following examples are intended to illustrate, but not to limit, the invention.

EXAMPLE 1

Purification and N-Terminal Sequencing of Coffee Bean α-Galactosidase

Coffee bean α-galactosidase manufactured by Boehringer Mannheim Biochemicals (BMB α-Gal) was initially analyzed by SDS-PAGE and found to contain about 40% of a 68 kD protein (BSA added as stabilizer); 35% of a 40 kD protein; 10% of a 36 kD protein; and 15% of several minor proteins including an approximately 26 kD protein (corresponding to the molecular weight for α-galactosidase from coffee bean previously reported).

For affinity chromatography, the commercial preparation containing 500 µg total protein in 500 µl was buffer-exchanged by centrifugal ultrafiltration (Centricon 30, Amicon) into 0.1×assay buffer. (1×buffer is 123 mM $Na_2HPO_4$, 37 mM citric acid, pH 6.0.) The sample was loaded onto a 1 ml melibiose-agarose column (Sigma) equilibrated with 0.1×assay buffer at 40° C., and one 0.5 ml fraction was collected. The α-Gal was eluted with 5 volumes of 1×assay buffer containing 15 mM p-nitrophenyl-α-D-galactoside (PNPG), and ten 0.5 ml fractions were collected. Fractions were analyzed for enzymatic activity and by SDS-PAGE. To assess enzymatic activity, 12.5 µl of each fraction was combined with 150 µl of 1×assay buffer containing 10 mM PNPG in a microtiter plate well, incubated for 1.5 hours at room temperature, and the optical density at 410 nm was determined in a microtiter plate reader.

The resulting elution pattern is shown in FIG. 2, as analyzed by SDS-PAGE of the fractions. Lane 1 represents molecular weight markers; lane 2, flow-through after binding; lanes 3–12, fractions collected during washing; lanes 13–17, fractions collected during elution; and lane 18, a sample of the BMB α-Gal starting material before application to the column. The fraction shown in lane 14, which contains essentially pure 40 kD protein, was determined to have the highest level of α-galactosidase activity.

A portion of the 40 kD protein purified in this way was subjected to N-terminal sequence determination using an Applied Biosystems 4778-120A Protein Sequencer, and the first 12 amino acids were determined. This sequence showed a high degree of homology to the corresponding guar protein and less homology to the human and yeast counterparts. The sequence obtained is identical to the first 12 amino acids shown as positions 1–12 in FIG. 1.

EXAMPLE 2

Preparation of Anti-α-Galactosidase Antibodies

Commercial coffee bean α-Gal (BMB) (300 µg) was buffer-exchanged (Centricon 30, Amicon) into phosphate buffered saline (PBS: 137 mM NaCl, 2.7 mM KCl, 4.3 mM $Na_2HPO_4$—$7H_2O$, 1.4 mM $KH_2PO_4$). The sample was electrophoresed through a 12% total (2.67% crosslink) SDS-polyacrylamide gel using standard conditions. The 40 kd protein band was visualized by soaking the gel in 0.1 M KCl at 4° C. for 15 minutes which precipitates the proteins in situ. The 40 kD α-Gal band was excised from the gel, transferred to a 1.5 ml microcentrifuge tube, and homogenized in 200 µl of PBS. The final mixture, 300 µl, contained approximately 120 µg of α-Gal.

Two Balb-C mice were each immunized intraperitoneally (IP) with 60 µg of the α-Gal preparation mixed 1:1 with complete Freund's adjuvant. Mice were boosted IP on day 14 and 28 with approximately 30 µg of isolated 40 kD band mixed 1:1 with incomplete Freund's adjuvant. Test bleeds (tail) were taken on day 21 and 35 to evaluate the titer of anti-α-Gal antibodies. Hyperimmune mouse ascites fluid (HMAF) was produced by injecting IP approximately $2 \times 10^8$ sarcoma 180 cells per mouse 15 days after the second boost. Ascites fluid was collected on days 8 and 12 postinduction. Test bleeds and HMAF were evaluated by Western blots of BMB coffee bean α-Gal transferred to Nitroplus 2000 membrane (Micron Separations, Inc.).

EXAMPLE 3

Analysis of α-Galactosidase Levels in Developing Coffee Beans

Fresh coffee fruits were separated into eleven developmental stages, 1 to 11. Stages 1–5 contain no, ¼ full, ½ full, ¾ full and full endosperm, respectively, as graded by inspection of seed endosperm after taking a center cross-sectional cut through the green cherries. Stages 6–10 are based on visible ripening of the fruit wherein the epicarp (skin) progresses from green-yellow (stage 6) to yellow-green (stage 7) to yellow (stage 8) to yellow-red (stage 9) to red (stage 10), and stage 11 represents fully mature cherries dried in the field, roughly equivalent to the harvested and dried fruit used for roasting.

The pulp (mesocarp) and parchment (endocarp) were removed from four beans (two fruits) per developmental stage, and the beans were sliced into 8 to 10 cross sections and incubated in PBS for 2 hours on ice. The extracts were then cleared by centrifugation at 5,000×g at 4° C. for 5 minutes. Samples representing 1/200th of each extract were prepared for SDS-PAGE and Western blot analysis by mixing with protein sample buffer and boiling for 3 minutes.

Western blots were blocked with Tris-buffered saline/tween 20/milk (TBST-milk: 150 mM NaCl, 10 mM Tris-Cl, pH 8.0, 0.05% tween 20, 1% nonfat powdered milk) for 1 hour, incubated with a 1:800 dilution of the anti-α-Gal HMAF described in Example 2 in TBST-milk for 1 hour, washed with TBST, incubated with a 1:7500 dilution of goat anti-mouse alkaline phosphate-conjugated antibody (Promega) in TBST-milk for 45 minutes, washed with TBST, and reacted with substrate (BCIP and NBT, Promega) according to the manufacturer's recommendations.

Figure 3:
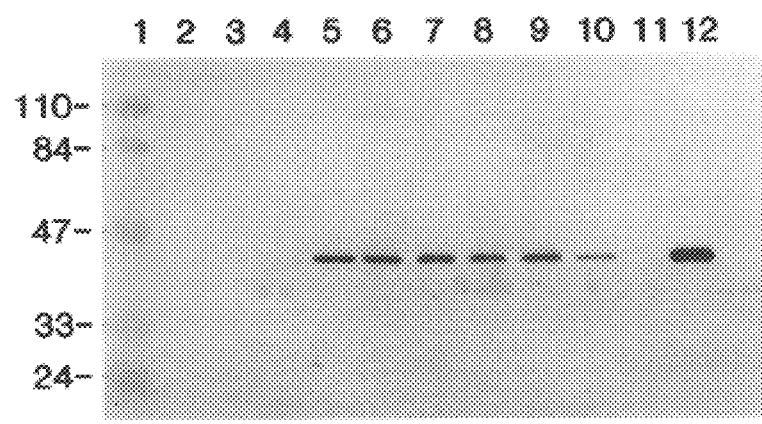
FIG. 3 shows a series of Western blots monitoring the expression of the α-galactosidase gene in developing coffee beans.

FIG. 3 shows the results of this Western blot analysis. Lane 1 contains molecular weight markers; lane 2 is blank; lanes 3–10 represent developmental stages 4–11; lane 11 is blank; and lane 12 is commercial coffee bean α-galactosidase. No α-galactosidase was detected in stages 1–4; the enzyme was first detected in stages 5–6; the peak activity appeared at stages 6 and 7.

EXAMPLE 4

Isolation of α-Galactosidase-Encoding RNA

RNA was extracted from stages 5 and 6 coffee beans using a modification of the method of Georgini, J. F., *Brazilian J Med Biol Res* (1988) 21:811–824.

For each isolation two hundred coffee beans (100 fruits, approximately 50 g) were peeled and immediately frozen in liquid nitrogen, then partially thawed at room temperature and 120 ml of room temperature TES extraction buffer (200 mM Tris-Cl, pH 7.5, 10 mM EDTA, 1% SDS) was added. When fully thawed (temperature kept below 4°C.), the beans were ground in a Sorvall omnimixer for 1.5 minutes on setting 6, and then homogenized with a Polytron homogenizer using six 15 second pulses at setting 6. The homogenate was filtered through miracloth (Calbiochem) and divided into six aliquots. Each aliquot was extracted with a half volume of TES-buffered phenol, and the phases were separated by centrifugation at 25,000×g for 10 minutes. The aqueous phase from each aliquot was mixed with an equal volume of CsCl solution (100% w/v, density approximately 1.7 g/ml), and the RNA was then pelleted through a cushion of CsCl.

The cushions were set up as follows: 10 ml of 100% (w/v) CsCl solution was added to a polyallomer centrifuge tube, and 28.5 ml of the coffee bean extract-CsCl solution was carefully overlaid. The gradients were centrifuged in a Beckman SW28 rotor at 25,000 rpm for 18 hours at 20° C. The resulting RNA pellets were dissolved in 0.3 M NaOAc and precipitated with two volumes of ethanol. The RNA was collected by centrifugation, dissolved in 100 µl of water, and quantitated by UV spectrophotometry.

Poly(A)$^+$ RNA was prepared using Promega's PolyATract magnetic sphere kit. Approximately 1 mg of total RNA was used in a small scale isolation protocol provided by the manufacturer. The resulting poly(A)$^+$ RNA was quantitated by UV spectrophotometry. Typical yields for each 200-bean preparation were about 1.5 mg of total RNA containing about 0.5–0.6% polyadenylated RNA. The quality of total and poly(A)$^+$ RNA was evaluated by standard MOPS/EDTA-formaldehyde gel electrophoresis using 0.66 M formaldehyde.

Poly(A)$^+$ RNA was also evaluated by reverse transcription assays performed in a 60 µl volume containing 1 µg of poly(A)$^+$ RNA, 12 µl 5×buffer (Bethesda Research Laboratories, BRL), 15 units RNasin (Pharmacia), 500 µM each dNTPs, 25 µCi α$^{32}$P-dCTP, 100 pmole oligo-d(T) primer, and 400 units of M-MLV reverse transcriptase (BRL). The reaction was incubated at 37° C. for 10 min with all components minus enzyme, then for 30 min at 37° C. with enzyme, and stopped by cooling on ice. Control reactions contained 1.5 µg of purified globin mRNA (BRL). The percent incorporation was determined by counting total and bound counts on DEAE membrane (Schleicher and Schuell, NA45). The isolated coffee bean MRNA gave $^{32}$P-incorporation of about 0.6% of label versus about 2.5% in control reactions with purified globin mRNA.

EXAMPLE 5

Construction and Screening of a cDNA Expression Library

Approximately 3.5 µg of poly(A$^+$)RNA prepared from stages 5 and 6 was used to construct an expression library lambda in vector UniZAPII (Stratagene), using the ZAP-cDNA synthesis Kit (Stratagene). The kit synthesizes 1st strand cDNA using an oligo-d(T) primer/adaptor (which contains an unmethylated XhoI site), M-MLV reverse transcriptase, and 5-methyl-dCTP. Synthesis of 2nd strand cDNA is based on the RNase H procedure described by Gubler and Hoffman, *Gene* (1985) 25:263. Following 2nd strand synthesis, EcoRI adaptors were added, and the cDNA was digested with XhoI. Methylated XhoI sites are resistant to XhoI cleavage. Incorporation of the EcoRI and XhoI sites enables directional cloning. The synthesized cDNA was size fractionated on a sephacryl S-400 (Pharmacia) spin column and ligated to vector DNA. The ligated DNAs were packaged with Gigapack II Gold lambda phage extracts (Stratagene) and, subsequently titered using *E. coli* strain PLK-F' (Stratagene) which is capable of accepting methylated cDNA. The primary library was amplified in *E. coli* PLK-F' by plating approximately $1 \times 10^5$ pfu on each of ten 150 mm plates and eluting the resulting phage from the plates.

Eleven phage were randomly picked from the library and determined to contain inserts using the polymerase chain reaction (PCR) with primers (pUC forward and reverse) that flank the multiple cloning sites in the vector. The average size of the inserts was approximately 700 bp. Amplification of the primary library resulted in a titer of $1 \times 10^{10}$ pfu/ml.

A total of $6 \times 10^5$ pfu from the amplified library were plated with the *E. coli* strain XL-1-blue (Stratagene) on twelve 150 mm plates and screened with the anti-α-galactosidase antibody of Example 2. The plates were incubated at 42° C. for 4 hours, expression of cDNA inserts was induced by placing membranes (Nitroplus 2000, 0.45 µm, Micron Separations, Inc.) previously soaked in 10 mM IPTG on the plates. After incubating at 37° C. for 3.5 hours, the first filter was removed, and a second IPTG-soaked filter was placed on the plate, incubated at 37° C. for 5.5 hours, and then removed. Filters were rinsed in TBST for approximately 1 minute, air dried, and stored in 4° C. overnight.

The filters were immunoprobed using a 1:500 dilution of the anti-α-Gal antiserum that was preadsorbed with an *E. coli* extract (Stratagene) as recommended by the manufacturer. All steps of the immunoscreening procedure were carried out at room temperature using approximately 10 ml of solution per filter (100 ml total). The procedures for immunoscreening the library were the same as described above for Western blots.

Immunoscreening of $6 \times 10^5$ pfu from the amplified library with the anti-α-Gal HMAF identified eleven plaques that were positive on duplicate filters. Following one round of plaque purification, five of the eleven were positive and were plaque purified a second time. The insert sizes of the five isolated phage were determined by PCR amplification using pUC forward and reverse sequencing primers. Four of the five clones contain an insert of approximately 1500 bp, and the fifth clone contains an insert of approximately 700 bp.

In order to rapidly confirm the identity of the isolated clones, we used a degenerate oligonucleotide (comprising 256 sequences) corresponding to what we identified as the largest conserved amino acid sequence (Gly-Gly-Trp-Asn-Asp, GGWND) among the guar, yeast, and human α-Gal sequences. The GGWND oligo (primes the sense strand) was used in combination with a pUC forward sequencing primer (primes the antisense strand) for PCR amplification of the 3' end of cDNA. Three clones were used as templates for PCR amplification, one 1500 bp insert clone, the 700 bp insert clone, and a randomly picked, non-immunoreactive clone. Assuming that the coffee-α-Gal primary structure is homologous to that of guar α-Gal and contains the GGWND sequence, we expected a PCR product of approximately 700 bp from clones not truncated at the 3' end. Both the short and long immunoreactive clones yielded an amplification product of the predicted size, while the randomly picked, non-immunoreactive clone did not. These results support the interpretation that the immunoreactive cDNA clones encode coffee α-Gal. If so, the 1500 bp inserts are of sufficient size to encode a 40 kD protein and potentially represent full-length coffee α-Gal cDNA clones. The production of a PCR product by the 700 bp cDNA insert of a size indistinguishable from the PCR product generated by the 1500 bp cDNA suggests that the shorter insert is an α-Gal cDNA truncated at its 5' end.

Following two rounds of plaque purification, recombinant phagemids (pBluescriptSK +/−) were excised from the lambda clones by coinfection with helper phage as described by the manufacturer. Bacteria (XL1-Blue) containing rescued phagemids were single colony purified. Inserts were released from all five recovered phagemids after EcoRI-XhoI double digestion, and as previously determined by PCR analysis, four of the five inserts were of the same size, approximately 1500 bp, and the fifth clone contained a smaller insert of approximately 700 bp. The five plasmids are referred to as p27αgA1-1, p27αgC1-1, p27αgE1-1, p27αgH1-1 (700 bp insert), and p27αgH2-3. Restriction enzyme analysis demonstrated that the large inserts contain a unique HindIII site approximately 500 bp from the 5' end of the insert and a unique PstI site approximately 300 bp from the 3' end. The short clone also contains a similarly positioned PstI site, but lacks the HindIII site. Based on the PCR results with the GGWND oligo and the restriction enzyme analysis, the 700 bp clone appeared to represent a 5' truncated version of the coffee α-Gal cDNA, possibly formed by premature termination during the first strand cDNA synthesis

EXAMPLE 6

Nucleotide Sequence Determination and Analysis

Figure 4:
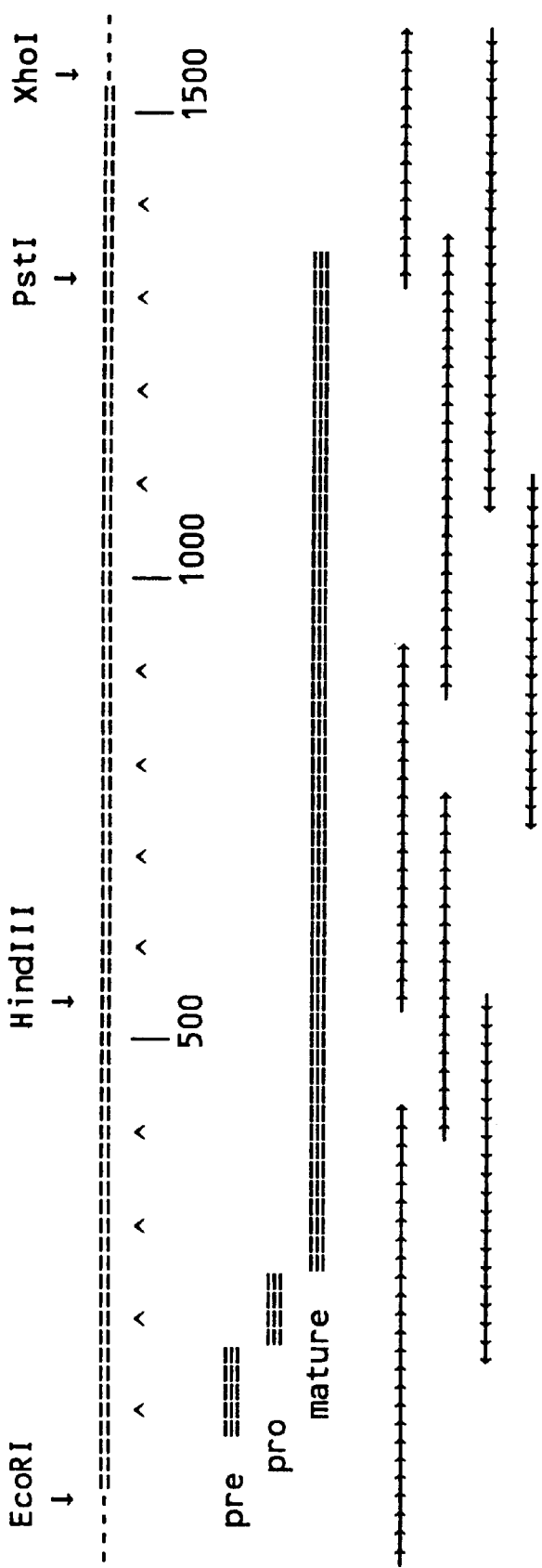
FIG. 4 shows a diagram of the sequencing strategy for α-galactosidase cDNA.

Nucleotide sequence of one of the 1500 bp inserts, clone p27αgC1-1, was determined. We obtained double stranded sequence of this clone with the exception of 180 protein-encoding nucleotides (540–720) and the untranslated leader, where sequence was obtained from a single strand. The other three clones containing 1500 bp inserts were partially sequenced, and we observed no differences except for the position of the 5' end of the cDNAs. To facilitate the sequencing of the clone p27αGC1-1, the unique HindIII and PstI site were used to generate subclones. We used a combination of pUC forward and reverse primers and insert-specific primers to sequence p27αgC1-1 and the subclones. The sequencing strategy is shown in FIG. 4.

The complete sequence and deduced amino acid sequence is shown in FIG. 1. The 6 cysteines potentially involved in disulfide formation are underlined. The potential polyadenylation signal (AAT AAA) is underlined. The potential glycosylation site is overscored by +++.

What is claimed is:

1. A composition of DNA molecules consisting of DNA molecules encoding coffee bean α-galactosidase of the amino acid sequence shown as amino acids 1–363 in SEQ ID NO:2 or an amino acid sequence encoded by an allelic variant of the nucleotide sequence of SEQ ID NO:1.

2. A recombinant expression system capable, when contained in a host cell, of expressing a DNA encoding a protein having coffee bean α-galactosidase activity, which expression system comprises a nucleotide sequence encoding a coffee bean α-galactosidase having the amino acid sequence numbered 1–363 in SEQ ID NO:2, or an allelic variant of the nucleotide sequence of SEQ ID NO:1 operably linked to control sequences compatible with said host cell.

3. A host cell modified to contain the expression system of claim 2.

4. A method to produce coffee bean α-galactosidase, which method comprises culturing the cells of claim 3 under conditions wherein said encoding nucleotide sequence is expressed to produce said coffee bean α-galactosidase; and recovering said coffee bean α-galactosidase from the culture.

5. An oligonucleotide which is the complement of the nucleotide sequence of SEQ ID NO:1 or of a portion thereof.

6. An oligonucleotide capable of forming a triplex with a double stranded DNA comprising the nucleotide sequence of SEQ ID NO:1 and its complement.

7. An oligonucleotide capable of forming a triplex with a double stranded DNA comprising the DNA region which effects expression of the protein-encoding region of the nucleotide sequence of SEQ ID NO:1.

* * * * *